United States Patent [19]

Shuttleworth

[11] 3,960,938

[45] June 1, 1976

[54] EXTRACTION OF SULFURIC ACID FROM SULFURIC ACID-SULFONIC ACID MIXTURES

[75] Inventor: Henry Shuttleworth, Trinidad, British W. Indies

[73] Assignee: Texaco Trinidad, Inc., Trinidad, British W. Indies

[22] Filed: Mar. 1, 1971

[21] Appl. No.: 120,068

[52] U.S. Cl. .............................................. 260/504 S
[51] Int. Cl.² ........................................ C07C 139/00
[58] Field of Search ................................. 260/504 S

[56] References Cited
UNITED STATES PATENTS

| | | | |
|---|---|---|---|
| 513,204 | 1/1894 | Schroter | 260/505 |
| 3,056,831 | 10/1962 | Stratford | 260/505 |

OTHER PUBLICATIONS

Gilbert, "Sulfonation and Related Reactions," (1965), pp. 131–134.

Primary Examiner—James O. Thomas, Jr.
Assistant Examiner—A. Siegel
Attorney, Agent, or Firm—T. H. Whaley; C. G. Ries; Henry W. Archer

[57] ABSTRACT

Sulfuric acid is substantially completely removed from mixtures in which it occurs together with sulfonic acids by extraction with concentrated hydrochloric acid. The extraction can be carried out countercurrent wise with from 50 to 150 volume percent of hydrochloric acid, depending on the number of stages used. This process is particularly useful for removing sulfuric acid from the heavy product phase resulting from the sulfoxidation of paraffins.

7 Claims, No Drawings

EXTRACTION OF SULFURIC ACID FROM SULFURIC ACID-SULFONIC ACID MIXTURES

BACKGROUND OF THE INVENTION

1. Field of the Invention

This invention relates to a process for removing sulfuric acid found in the product from a sulfoxidation process by extraction with concentrated hydrochloric acid.

2. Description of the Prior Art

In commonly assigned co-pending application, Ser. No. 40,740, filed May 26, 1970, there is disclosed and claimed a process for producing sulfonic acid without irradiation by reacting in a reactor substantially straight chain saturated liquid hydrocarbons with oxygen and sulfur dioxide under substantially anhydrous conditions in the presence of a low molecular weight acyl oxide such as acetic anhydride at temperatures of about 25° to 55°C. under pressures of from 0 to 100 psig while agitating throughout the process these reactants followed by continuously removing the resulting heavy phase containing product and unreacted paraffins from the reactor.

The linear sulfonate product prepared by this process contains about 35 mole percent of sulfuric acid. Although this quantity of sulfuric acid is high, it has no detrimental effect in a finished detergent formulation containing such sulfonates as the sodium sulfate formed from the sulfuric acid can be used as part of the "builders" in the detergent. Undesirably, it is not possible with this high a sulfuric acid content to obtain aqueous solutions of a neutral mixture at concentrations greater than 30% w/w owing to the separation of sodium sulfate at room temperature. Thus it would be advantageous with regards to increased facility in handling, improvement of minimum product value and appearance, if the sulfuric acid content could be reduced economically. Similarly, it would improve the economics of the process if the sulfuric acid could be made readily available for producing sulfur dioxide which could be used again in the sulfoxidation reaction.

SUMMARY OF THE INVENTION

The heavy product phase from the sulfoxidation reaction contains mono- and di-sulfonic acids, sulfuric acid, unreacted paraffin hydrocarbons, acetic acid, water and sulfur dioxide. This phase is contacted with from about 0.1 to about 10 volumes of concentrated hydrochloric acid at room temperature in a separating funnel. Separation into two clearly defined phases is complete in approximately 15 minutes. The bottom phase is the hydrochloric acid phase and contains some of the sulfuric acid from the heavy product phase as well as a little of the sulfonic acids and the acetic acid. In addition, some of the colored impurities are extracted together with the sulfuric acid. After running off the hydrochloric acid phase, the top phase is again contacted with fresh hydrochloric acid. The concentrated hydrochloric acid can be removed from the extracted sulfonic acids at about 50°C under a vacuum pressure less than about 50 mms. of mercury. It is preferred, in particular, in large scale operations, to first remove sulfur dioxide from the heavy product phase by degassing this phase at about 0°C with a stream of an inert gas such as nitrogen.

DESCRIPTION OF SPECIFIC EMBODIMENTS

A preferred four-stage extraction process is carried out in the following manner: 50 parts by volume of heavy product phase was shaken with 50 parts by volume of concentrated hydrochloric acid solvent in each one of four separating funnels. After allowing the phases to separate, the hydrochloric acid was run off from each separator, this solvent layer was then charged to the adjacent separator in line. Hydrochloric acid solvent therefore travelled in one direction through the four separators and heavy product phase passed the other way. Fresh 50 parts by volume charges of both heavy product phase and hydrochloric acid were introduced at opposite ends of the system and spent hydrochloric acid solvent and extracted heavy product phase were taken off. After passing eight charges of hydrochloric acid solvent and heavy product phase through the system, this batchwise counter-current extraction had settled down to "steady state" conditions. Analyses carried out on the spent hydrochloric acid solvent stream showed a constancy of composition after the sixth extraction confirming the system's equilibrium. After the ninth extraction the individual streams were completely analysed.

Analysis of all samples was carried out by the aniline method. To a suitably sized sample (2 parts by volume of hydrochloric acid phase or 1 part by volume of the heavy product phase) was added 15 parts by volume aniline and 100 parts by volume benzene. The mixture was azeotroped dry and then filtered through a sintered glass crucible. After washing the precipitate with hot dry benzene, the filtrate and precipitate were separately titrated with standard caustic to phenol phthalein end point. The filtrate titration gave the equivalents of sulfonic acid directly. The solution after titrating the precipitate was analyzed for chloride and sulfate ions.

A sample of heavy product phase obtained from paraffin sulfoxidation was extracted three times with an equal volume of concentrated hydrochloric acid (35% w/w) solvent at room temperature. Details of this extraction are given in Table I and illustrate diagrammatically the volume changes throughout the extractions. The analyses show that 93% of the sulfuric acid has been extracted from the heavy product phase at the expense of 21% of the sulfonic acids. The analyses reveal that the sulfonic acid has a constant solubility in the hydrochloric acid solvent whereas the sulfuric acid partitions between the phases. The sulfonic acid was later isolated from the hydrochloric acid phase and shown to be mainly disulfonic acid (97%).

TABLE I

CONCENTRATED HYDROCHLORIC ACID SOLVENT EXTRACTION
OF HEAVY PRODUCT PHASE FROM THE SULFOXIDATION REACTION

| | Parts by Volume | Acid equivalents (g. mole) | | |
|---|---|---|---|---|
| | | Sulfonic | Sulfuric | Hydrochloric |
| Heavy product phase ↓ | 150 | | | |
| Hydro- | | | | |

TABLE I-continued

CONCENTRATED HYDROCHLORIC ACID SOLVENT EXTRACTION OF HEAVY PRODUCT PHASE FROM THE SULFOXIDATION REACTION

| | | Parts by Volume | Acid equivalents (g. mole) | | |
|---|---|---|---|---|---|
| | | | Sulfonic | Sulfuric | Hydrochloric |
| chloric acid | 1st Extraction → Extract A | 150 | | | |
| | ↓ | 115 | 0.046 | 0.274 | 1.134 |
| Hydro-chloric acid | 2nd Extraction → Extract B | 150 | | | |
| | ↓ | 176 | 0.045 | 0.118 | 1.928 |
| Hydro-chloric acid | 3rd Extraction → Extract C | 150 | | | |
| | ↓ | 164 | 0.041 | 0.037 | 1.734 |
| | Final Product | 164 | 0.492 | 0.033 | 0.303 |
| | Total | | 0.624 | 0.462 | |

The effect of the hydrochloric acid solvent/heavy phase ratio was compared at three values viz. 1.0, 0.83 and 0.67. These results are presented in the table below and show that little separation of the phases occurs at the lowest value. The sulfuric acid/sulfonic acid ratio in the hydrochloric acid phase is not apparently affected across the range of values selected. Actually, two phases are formed between water and the sulfonic/sulfuric acids mixture when the hydrochloric acid content of the water is greater than about 10% w/w. The sulfonic acids present in the aqueous phase are reduced to an acceptable level by increasing the concentration of hydrochloric acid to its maximum, at atmospheric pressure, of 35% w/w.

TABLE II

HYDROCHLORIC ACID EXTRACTIONS OF SULFURIC ACID FROM SULFOXIDATION HEAVY PHASE

| | Before H.P.* | Parts by vol. HCl | HCl/H.P. ratio, vol. | After H.P. | Parts by vol. HCl | HCl Phase Analysis H₂SO₄ (g. equivalents) | | | |
|---|---|---|---|---|---|---|---|---|---|
| | | | | | | HCl | H$_2$SO$_4$ | RSO$_3$H | RSO$_3$H |
| A. | 150 | 150 | 1 | 210 | 90 | 0.713 | 0.203 | 0.012 | 16.7 |
| B. | 150 | 125 | .83 | 235 | 40 | 0.297 | 0.111 | 0.011 | 10.0 |
| C. | 150 | 100 | .67 | 240 | 10 | 0.064 | 0.031 | 0.003 | 12.4 |

*Heavy phase composition of 150 parts by volume sample is:
Sulfonic acids 0.501 g. equivalents
Sulfuric acids 0.451 g. equivalents Four-stage counter-current extraction was set up as above described. Results are given with the practical details in Table III. It is seen from these results that 99.8% of the sulfuric acid present initially in the heavy product phase has been extracted at the expense of 4% of the sulfonic acids.

TABLE III

FOUR-STAGE CONCENTRATED HYDROCHLORIC ACID SOLVENT EXTRACTION OF HEAVY PRODUCT PHASE FROM THE SULFOXIDATION REACTION

| | Parts by Volume | Acids weight, parts by wt. | | |
|---|---|---|---|---|
| | | Sulfonic | Sulfuric | Hydrochloric |
| Hydrochloric acid | 50 | 0 | 0 | 20.5 |
| ↓ → Extracted heavy phase | 67 | 51.6 | 0.02 | 7.8 |
| 1st Stage | | | | |
| | 70 | 50.0 | 0.07 | N.D. |
| | 53 | 1.83 | 0.84 | N.D. |
| 2nd Stage | | | | |
| ↓ ↑ | 72 | 51.4 | 1.71 | N.D. |
| | 55 | 2.28 | 1.70 | N.D. |
| 3rd Stage | | | | |
| ↓ ↑ | 75 | 53.6 | 4.91 | N.D. |
| | 58 | 3.08 | 4.72 | N.D. |
| 4th Stage | | | | |
| ↓ ↑ — Heavy Product Phase | 50 | 53.8 | 5.79 | 0 |
| Spent hydrochloric acid | 33 | 1.98 | 5.77 | 12.7 |

N.D. Not determined

This sulfonic acid reduction can be reduced further by using a decreased solvent/heavy product phase ratio. If a lower ratio was used, then more than four theoretical stages would be required to achieve the same degree of sulfuric acid removal.

The heavy product phase after removal of sulfuric acid still contains some hydrochloric acid solvent. In order that no color degradation occurred in the sulfonic acids product, hydrochloric acid was removed by distillation under vacuum at 50°C. Complete removal was effected after an hour's distillation. The residual sulfonic acids were neutralized with sodium hydroxide before steam distilling off the unreacted paraffin.

As previously mentioned, it is preferred, in particular for large scale operations, to remove sulfur dioxide by degassing at around 0°C. Because the degassing operation using nitrogen takes up to 12 hours it is necessary to proceed at low temperatures. Where the color of the product is not important, degassing can be carried out at room temperature and rapidly. Generally, however, most of the sulfur dioxide in the heavy product phase is removed by the concentrated hydrochloric acid solvent and any sulfur dioxide remaining in the product is removed when the small amount of hydrochloric acid remaining in the heavy phase is distilled off under vacuum.

What is claimed is:

1. Process for removing sulfuric acid from a paraffin sulfoxidation reaction mixture of mono- and di-sulfonic acids, sulfuric acid, unreacted paraffin hydrocarbons, acetic acid, water and sulfur dioxide, comprising the steps of:
  repeatedly contacting said mixture with concentrated hydrochloric acid to form a raffinate phase containing sulfuric acid and a heavy product phase containing unreacted paraffin hydrocarbons, sulfonic acids, some hydrochloric acid solvent; separating said phases;
  removing said hydrochloric acid from said heavy product phase; neutralizing said sulfonic acids; and steam distilling said unreacted paraffin hydrocarbons.

2. The process as defined in claim 1, wherein said contacting consists of at least one counter-current extraction step.

3. The process as defined in claim 1, wherein the volume ratio of hydrochloric acid to said mixture ranges from above about 0.1 to about 10.0.

4. The process as defined in claim 1, wherein said hydrochloric acid is removed from said heavy product phase by vacuum distillation at a temperature of around 50°C.

5. The process as defined in claim 4, wherein said vacuum distillation is carried out under a pressure less than about 50 mms. of mercury.

6. The process as defined in claim 1, wherein said mixture is first degassed at a low temperature with a stream of an inert gas to remove sulfur dioxide therefrom.

7. The process as defined in claim 6, wherein said degassing takes place at a temperature of around 0°C.

* * * * *